(12) United States Patent
Oroskar et al.

(10) Patent No.: US 8,937,191 B2
(45) Date of Patent: Jan. 20, 2015

(54) RECOVERY OF HIGHLY PURE ALPHA-TOCOTRIENOL FROM CRUDE PALM OIL EXTRACT

(71) Applicant: OROCHEM Technologies, Inc., Lombard, IL (US)

(72) Inventors: Anil Oroskar, Oak Brook, IL (US); Deepak Sharma, Naperville, IL (US); Vanshidhar Singh, Chicago, IL (US); Anand Oroskar, Oak Brook, IL (US); Gautham Oroskar, Oak Brook, IL (US)

(73) Assignee: OROCHEM Technologies, Inc., Naperville, IL (US)

( * ) Notice: Subject to any disclaimer, the term of this patent is extended or adjusted under 35 U.S.C. 154(b) by 125 days.

(21) Appl. No.: 13/722,414

(22) Filed: Dec. 20, 2012

(65) Prior Publication Data

US 2014/0179933 A1    Jun. 26, 2014

(51) Int. Cl.
    *C07D 311/00*     (2006.01)
    *C07D 311/72*     (2006.01)

(52) U.S. Cl.
    CPC .................................. *C07D 311/72* (2013.01)
    USPC ....................................................... 549/413

(58) Field of Classification Search
    CPC ............................ C07D 311/72; C07D 311/22
    USPC ....................................................... 549/413
    See application file for complete search history.

(56) References Cited

U.S. PATENT DOCUMENTS

| | | |
|---|---|---|
| 2,985,589 A | 5/1961 | Broughton |
| 4,122,094 A | 10/1978 | Woziwodzki |
| 4,412,866 A | 11/1983 | Schoenrock |
| 5,102,553 A | 4/1992 | Kearney |
| 5,157,132 A | 10/1992 | Tan |
| 5,190,618 A | 3/1993 | Top |
| 5,908,940 A | 6/1999 | Lane |
| 6,093,326 A | 7/2000 | Heikkila |
| 6,187,204 B1 | 2/2001 | Heikkild |
| 6,379,554 B1 | 4/2002 | Kearney |
| 6,395,915 B1 | 5/2002 | Bellafiore |

(Continued)

OTHER PUBLICATIONS

Lu et al., "Stimulated moving bed separation of tocopherol homologues: simulation and experiments", Journal of Zhejiang University Science A (2009) 10(5), pp. 758-766 (China).

(Continued)

*Primary Examiner* — T. Victor Oh
(74) *Attorney, Agent, or Firm* — Richard P. Silverman & Assoc., LLC

(57) ABSTRACT

Disclosed is a process for the production of high purity alpha-tocotrienol from palm oil extract. More particularly, the invention relates to a process for the separation of alpha-tocotrienol from a mixtures of other tocotrienols and tocopherols and the use of a simplified separation scheme based on a combination of solid phase extraction and simulated moving bed (SMB) separation steps employing polar phase simulated moving bed operation. The process is useful for providing a continuous route and a simplified processing route to providing pure alpha-tocotrienol as a major product essentially free of other tocotrienols and tocopherols including: beta-tocopherol, gamma-tocotrienol, delta-tocotrienol, gamma-tocopherol, delta-tocopherol, front end and back end carotenoids, and alpha-tocopherol as a by-product from palm oil extract. Alpha-tocotrienol is a form of vitamin E and may be useful as a treatment for preventing stroke or reducing brain and nerve damage following a stroke.

15 Claims, 3 Drawing Sheets

(56) References Cited

U.S. PATENT DOCUMENTS

| | | |
|---|---|---|
| 7,667,061 B2 | 2/2010 | Binder |
| 8,106,223 B2 | 1/2012 | Wesson |
| 2010/0093530 A1 | 4/2010 | Binder |

OTHER PUBLICATIONS

Anna-Maija Lampi, "Analysis of Tocopherols and Tocotrienols by HPLC", The AOCS (American Oil Chemists' Society)Lipid Library, (Aug. 3, 2011) (US) available online at http://lipidlibrary.aocs.org/topics/tocopherols/index.htm.

Chandan K. Sen, et al., "Palm Oil—Derived Natural Vitamin E a-Tocotrienol in Brain Health and Disease", Journal of the American College of Nutrition, (2010) vol. 29, No. 3, 314S-323S, US.

Lu et al., "Simulated moving bed separation of tocopherol homologues: simulation and experiments", Journal of Zhejiang University Science A (2009) 10(5), pp. 758-766 (China).

RECOVERY OF HIGHLY PURE ALPHA-TOCOTRIENOL FROM CRUDE PALM OIL EXTRACT

FIELD OF THE INVENTION

This invention concerns generally with a process for the recovery and purification of alpha-tocotrienol from crude palm oil extract. More specifically, the invention relates to a process for the purification of alpha-tocotrienol in the presence of other isomers including tocotrienol, tocopherols, phytosterols, and carotenoids. More particularly, the invention relates to a process for the purification and continuous production of a pure alpha-tocotrienol using simulated moving bed technology.

BACKGROUND

Alpha-tocotrienol is a natural antioxidant and it protects glutamate-induced death of neuronal cells (brain cells). It is a member of Vitamin E family with 4 different isomers of trienols (alpha, beta, gamma, and delta) and 4 different isomers of pherols (alpha, beta, gamma, and delta). Alpha-tocotrienol has the following structure:

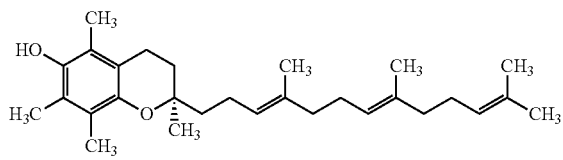 [SMILES: CC(C)=CCC/C(C)=C/CC/C(C)=C/CC[C@]1(C)CCc2c(C)c(O)c(C)c(C)c2O1]

Tocotrienols occur largely in palm oil extract, rice bran oil, and barley. While synthetic and natural tocopherols are readily available in the market, the supply of natural tocotrienols is limited, and generally comprises a mixture of tocotrienols. Crude palm oil extract which is rich in tocotrienols (800-1500 ppm) offers a potential source of natural tocotrienols. Carotech, located in Malaysia, is an industrial plant able to extract and concentrate tocotrienols from crude palm oil extract. Carotech uses a molecular distillation process (employing ultra-high vacuum and very low temperature) in its production plant. This process (see U.S. Pat. No. 5,157,132) allows Carotech to extract phytonutrients such as the Tocotrienol Complex (TOCOMIN™, a registered trademark of Carotech for extracts and concentrates of palm tree fruits) from the crude palm oil extract. TOCOMIN™-50 typically comprises about 25.32% mixed tocotrienols (7.00% alpha-tocotrienol, 14.42% gamma tocotrienol, 3.30% delta tocotrienol and 0.6% beta tocotrienol), 6.90% alpha-tocopherol and other phytonutrients such as plant squalene, phytosterols, co-enzyme Q10 and mixed carotenoids.

Methods of purification of component of alpha-tocotrienol from palm oil extract have been disclosed in literature, but such methods comprise either separating all the isomers of tocotrienols from the remaining tocopherols or using a complex series of reactions to convert other forms of trienols to the alpha form.

Methods of purification of alpha tocotrienol in small amounts have been disclosed using reverse phase chromatography in conjunction with a C18 adsorbent. Such methods have not proved to be economical for commercial scale production. For examples of such reverse phase chromatographic methods see U.S. Pat. No. 4,122,094; U.S. Pat. No. 5,190,618 and U.S. Pat. No. 5,908,940. More recently, U.S. Pat. No. 8,106,223 discloses methods of the production, enrichment and isolation of pure alpha-totrienol by a combination of functionalization of non-alphatocols by reaction and extraction from source material comprising at least one tocotrienol which is not alpha-tocotrienol.

Simulation of a moving sorbent bed is described in U.S. Pat. No. 2,985,589 (Broughton et al.), which is mentioned above. In accomplishing this simulation, it is necessary to connect a feed stream to a series of beds in sequence, first to bed no. 1, then to bed no. 2, and so forth for numerous beds, the number of beds often being between 12 and 24. These beds may be considered to be portions of a single large bed whose movement is simulated. Each time the feed stream destination is changed, it is also necessary to change the destinations (or origins) of at least three other streams, which may be streams entering the beds, such as the feed stream, or leaving the beds. The moving bed simulation may be imply described as dividing the bed into series of fixed beds and moving the points of introducing and withdrawing liquid streams past the series of fixed beds instead of moving the beds past the introduction and withdrawal points. A rotary valve used in the Broughton process may be described as accomplishing the simultaneous interconnection of two separate groups of conduits.

U.S. Pat. No. 4,412,866 describes an example of the operation of chromatographic simulated moving bed (or sometimes called "SMB") method to separate the components of a feedstock. A resin bed is divided into a series of discrete vessels, each of which functions as a zone within a circulation loop. A manifold system connects the vessels and directs, in appropriate sequence to (or from) each vessel, each of the four media accommodated by the process. Those media are generally referred to as feed stock, eluent, extract and raffinate, respectively. As applied to a sugar factory, a typical feed stock is a lower purity sucrose solution, the eluent is water, the extract is an aqueous solution of sucrose and the raffinate is an aqueous solution containing non-sucrose, such as salts and high molecular weight compounds. The simulated moving bed disclosed by the '866 patent is of the type sometimes referred to as a "continuous SMB."

Examples of simulated moving bed processes are disclosed, for instance, in U.S. Pat. No. 6,379,554 (method of displacement chromatography); U.S. Pat. No. 5,102,553 (time variable simulated moving bed process), U.S. Pat. No. 6,093,326 (single train, sequential simulated moving bed process); and U.S. Pat. No. 6,187,204 (same), each of the contents of the entirety of which is incorporated herein by this reference.

Methods are sought for a more efficient method of producing alpha-tocotrienol in pure form from palm oil extract and in a continuous production process with minimum processing steps and at low cost.

SUMMARY OF THE INVENTION

Applicant's invention relates to the a process for the recovery and purification of alpha-tocotrienol from crude palm oil extract. Applicant discovered that alpha-tocotrienol can be efficiently and selectively produced by the use of simulated moving bed separation (SMB) process employing a selective stationary phase adsorbent and a complimentary mobile phase desorbent in an effective SMB cycle.

In one embodiment, the invention is a continuous simulated moving bed separation process for the production of a high purity alpha-tocotrienol product stream from crude palm oil extract. The process comprises:

a. diluting the crude palm oil extract comprising front end carotenoids, alpha-tocopherol, alpha-tocotrienol, gamma-tocopherol, gamma-tocotrienol, beta-tocopherol, delta-tocopherol, delta-tocotrienol, and back end carotenoids in a non-polar solvent to provide a feed stream comprising 20 to 25 wt-% of the crude palm oil extract, b. passing the feed stream to a first solid phase extraction zone and therein contacting a first solid phase adsorbent comprising silica for the adsorption of back end carotenoids to remove at least a portion of the back end carotenoids from the feed stream provide a first SMB feed stream;

c. passing the first SMB feed stream to a first SMB zone comprising a plurality of adsorbent beds, each adsorbent bed containing a stationary phase agent comprising silica or alumina and passing a first mobile phase desorbent stream comprising non-polar solvent and a polar organic solvent in a first SMB zone ratio of from 80-99 parts non-polar solvent: 1-20 parts of the polar organic solvent to the first SMB zone to provide a first extract stream comprising non-polar solvent, polar organic solvent, back end carotenoids, gamma-tocotrienol, delta-tocotrienol, and gamma-tocopherol, and a first raffinate stream comprising non-polar solvent, organic polar solvent, front end carotenoids, alpha-tocopherol and alpha-tocotrienol;

d. passing the first raffinate stream to a first evaporization zone to remove essentially all of the polar organic solvent from the first raffinate stream to provide a first solvent stream comprising the polar organic solvent and an evaporated first raffinate stream and diluting the evaporated first raffinate stream with non-polar solvent to provide a second SMB feed stream comprising 3 to 10 wt-% of the evaporated first raffinate stream in non-polar solvent;

e. passing the second SMB feed stream to a second SMB zone comprising a plurality of adsorbent beds, each adsorbent bed containing a second stationary phase agent comprising silica or alumina and passing a second mobile phase desorbent stream comprising non-polar solvent and the polar organic solvent in a second SMB zone ratio of from 90-99 parts non-polar solvent: 1-10 parts of the polar organic solvent to the second SMB zone to provide a second raffinate stream comprising non-polar solvent, polar organic solvent, front end carotenoids, alpha-tocopherol, and to provide a second extract stream comprising non-polar solvent, polar organic solvent and alpha-tocotrienol;

f. passing the second extract stream to a second evaporization zone to remove essentially all of the polar organic solvent from the second extract stream to provide a second solvent stream comprising the polar organic solvent and an evaporated second extract stream and diluting the evaporated second extract stream with non-polar solvent to provide a diluted evaporated second extract stream comprising 5 to 15 wt-% of the evaporated second extract stream in non-polar solvent; and, g. passing the diluted evaporated second extract stream to a second solid phase extraction zone and therein contacting a basic alumina adsorbent to provide a first high purity alpha-tocotrienol stream comprising the non-polar solvent and alpha-tocotrienol;

h. terminating the passing of the diluted evaporated second extract stream to the second solid phase extraction zone and purging the second solid phase extraction zone in a first purging step with the non-polar solvent to provide a second high purity alpha-tocotrienol stream comprising the non-polar solvent and alpha-tocotrienol;

i. terminating the first purging step and purging the second solid phase extraction zone in a second purging step with the polar solvent to provide a byproduct stream comprising beta-tocopherol; and, j. combining the first and second high purity alpha-tocotrienol streams and removing the non-polar solvent to provide the high purity alpha-tocotrienol product stream having an alpha-tocotrienol purity of greater than or equal to 95 wt-% on a solvent free basis, wherein the non-polar solvent is hexane or n-heptane, and the polar organic solvent is isopropanol, ethanol, or ethyl-acetate.

BRIEF DESCRIPTION OF THE DRAWINGS

The following drawings are illustrative of the embodiments of the invention and are not meant to limit the scope of the invention in any way.

DETAILED DESCRIPTION OF THE INVENTION

Figure 1:
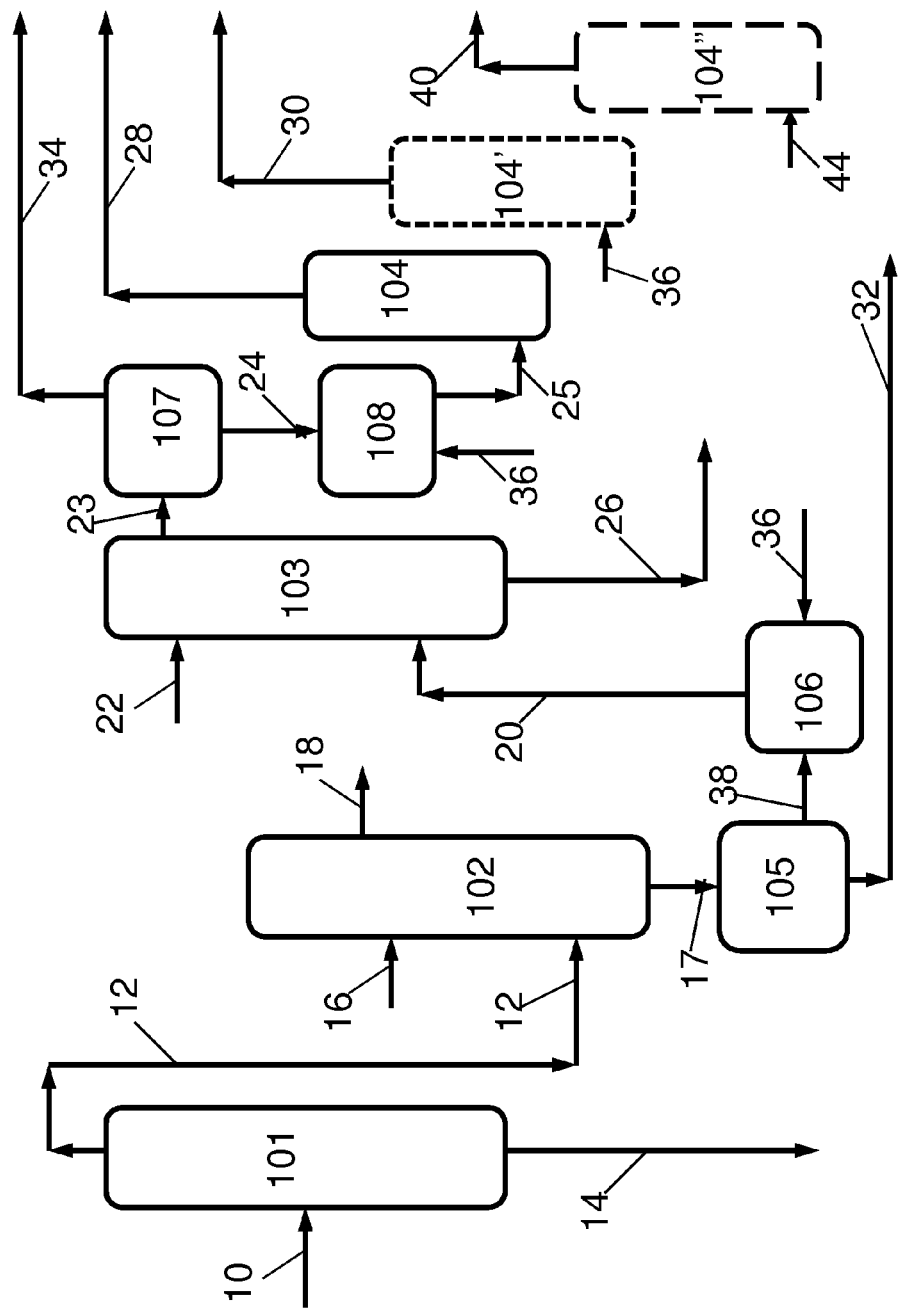
FIG. 1 is a schematic flow diagram illustrating one embodiment of the present invention.

Alpha-tocotrienol is typically present in palm oil extract in concentrations of between about 9 and about 12 percent by weight of the crude palm oil extract. The crude palm oil extract comprises various isomers of tocotrienol, tocopherols, phytosterols, and carotenoids. More specifically, the crude feed stream will comprise about 11 or 12 percent by weight of the crude palm oil extract.

The SMB system of the current invention was arranged for maximum selectivity for polar phase simulated moving bed operation. As used herein, polar phase simulated moving bed refers to an SMB which uses silica or alumina as the adsorbent and non-polar solvents like n-heptane as mobile phase desorbents. The simulated moving bed operation is achieved by use of a plurality of adsorbent beds connected in series and a complex valve system, whereby the complex valve system facilitates switching at regular intervals the feed entry in one direction, the mobile phase desorbent entry in the opposite direction, while changing the extract and raffinate takeoff positions as well. The SMB system is a continuous process. Feed enters and extract and raffinate streams are withdrawn continuously at substantially constant compositions. The overall operation is equivalent in performance to an operation wherein the fluid and solid are contacted in a continuous countercurrent manner, without the actual movement of the solid, or stationary phase adsorbent. In the present invention, it was necessary to employ two SMB zones operating with different mobile phases and using different selective adsorbents as the stationary phase agents. A first SMB zone operated in a rejection mode using a first stationary phase agent and a first mobile phase desorbent, and a second SMB zone operated in an extraction mode using a second stationary phase agent and a second mobile phase desorbent. The raffinate produced by the first SMB zone being rich in alpha-tocotrienol was evaporated to remove essentially all of the first mobile phase desorbent and then diluted with n-heptane prior to being passed to the second SMB zone.

Mobile Phase Desorbent

The mobile phase desorbent of the present invention is a polar binary solvent mixture comprising any proportion of a non-polar solvent, such as n-heptane or hexane, and a polar organic solvent. The polar organic solvent may be an alcohol or an acetate having from 2 to 4 carbon atoms. The polar organic solvent can be selected from the group consisting of ethanol, isopropanol, and ethyl-acetate. Preferably, the mobile phase desorbent is a polar binary mixture in any proportion selected from the group consisting of n-heptane: ethyl-acetate, n-heptane: isopropyl alcohol, and n-heptane: ethanol. Preferably, the desorbent is a binary mixture of n-heptane and polar organic solvent comprising about 80 to 99 parts n-heptane and 20 to 1 parts polar organic solvent. More preferably, the mobile phase desorbent is a binary mixture of n-heptane and polar organic solvent in a ratio of 80:20, 85:15, 90:10, 91:9, 92:8, 93:7, 94:6, or 95:5 parts n-heptane to parts polar organic solvent. It was discovered that there was particular advantage to employing different mobile phase desorbents at different points in the overall process. In a first SMB zone wherein the objective was to recover the alpha-tocotrienol rich material in the first raffinate, a first mobile phase desorbent having from 80 to 85 parts n-heptane to 15-20 parts polar organic compound such as ethyl-acetate was preferred. In a second SMB zone which extracted the alpha-tocotrienol rich material at high purity from the first raffinate, a mobile phase having from 90-99 parts n-heptane to 10-1 parts organic polar solvent such as ethyl-acetate was preferred. As will be shown hereinbelow, it was critical for the recovery of pure alpha-tocotrienol without beta-tocotrienol impurities to remove essentially all of the first mobile phase desorbent from the first raffinate stream by evaporation and dilute the evaporated first raffinate stream with n-heptane prior to passing the diluted first raffinate stream to the second SMB zone. Most preferably, the second mobile phase desorbent is a binary mixture of n-heptane and ethyl-acetate employed in the second SMB zone in a ratio of about 93:7 parts n-heptane to parts ethyl-acetate Stationary Phase Agent The stationary phase agent or adsorbent of the present invention may be silica, or alumina. More particularly, the stationary phase agent or adsorbent may be an irregular silica having an average particle size of from 75-200 microns and a pore size of about 75 Angstroms such SILICYLE 75-200 micron (Available from SiliCyle, Quebec City (Quebec) CANADA), a spherical form of silica having a particle size of about 50 microns and a pore size of about 60 Angstroms, such as AGC Spherical Silica 50 um 60 A (Available from AGC Chemicals Americas, Inc., Exton, Pa.), or alumina basic, having a particle size ranging from about 32 to 63 microns. It is preferred that stationary phase agent have a particle size between 50 and 500 microns and have a porosity of from about 60 to about 130 Angstroms. More preferably, the particle size of the stationary phase agent ranged from 250 microns to 400 microns, and most preferably, the average particle size of the stationary phase agent ranged from 300 to 375 microns. The particles of the stationary phase agent may be irregularly shaped or spherical, or mixtures of irregular shaped and spherical shaped particles. It was discovered that different stationary phase agents in the first and in the second SMB zones. The stationary phase agent of the first SMB zone and the second SMB zone can be selected from the group consisting of silica and alumina in order to achieve the desired product quality of the highly pure alpha-tocotrienol product. The highly pure alpha-tocotrienol product required the removal of the beta-tocopherol species to a beta-tocopherol concentration which is less than 1.0 wt-% on a solvent free basis.

SMB Operating Conditions

The operation of the SMB system is carried out at a constant temperature within a plurality of adsorbent beds. Preferably, the adsorbent beds of the present invention operate at an SMB temperature of about 30° C. to about 65° C. More preferably, the SMB zones of the present invention operate at an SMB temperature of between about 55° C. to about 60° C. The feed stream is introduced and components are adsorbed and separated from each other within the adsorbent bed. A separate liquid, the mobile phase desorbent, is used to countercurrently displace the feed components from the pores of the stationary phase adsorbent. During the SMB cycle of the present invention, adsorbent beds are advanced through a desorption zone, a rectification zone, an adsorption zone, and a regeneration zone. Preferably, the SMB zones of the present invention contain at least 8 adsorbent beds. The description of the SMB cycle as a 2-3-2-1 cycle means that in the cycle, 2 adsorbent beds are in the desorption zone, 3 adsorbent beds are in the rectification zone, and 2 adsorbent beds are in the adsorption zone, and 1 bed is idle.

Applicant's process provides a continuous process for the production of high purity alpha-tocotrienol at high purity; i.e., where the purity of the alpha-tocotrienol is greater than or equal to about 95 wt-%. More preferably, applicant's process provides a continuous process for the production of alpha-tocotrienol having a purity of greater than or equal to about 98 wt-%, and most preferably, applicant's process provides a continuous process for the production of alpha-tocotrienol having a purity of greater than or equal to about 99 wt-%.

DETAILED DESCRIPTION OF THE DRAWINGS

The process of the present invention in one embodiment is illustrated in FIG. 1. According to FIG. 1, a crude palm oil extract stream, or feed stream in line 10 comprising front end carotenoids, alpha-tocopherol, alpha-tocotrienol, gamma-tocopherol, gamma-tocotrienol, beta-tocopherol, delta-tocopherol, delta-tocotrienol, and back end carotenoids and in a feed preparation step is first diluted to about 20 to about 25 wt-% in n-heptane and is introduced to a first solid phase extraction zone 101. In the first solid phase extraction zone 101, the feed stream is contacted with an adsorbent selective for the adsorption of the back end carotenoids to provide a first SMB feed stream in line 12, which is filtered and has a reduced amount of the back end carotenoids relative to the feed stream. Intermittently, the passing of the feed stream in line 10 to the first solid phase extraction zone 101 is terminated and the first solid phase extraction zone 101 is flushed with a polar solvent such as isopropyl alcohol, ethanol or ethyl-acetate, having a purity of greater than or equal to 99 wt-%, to strip the back end carotenoids from the selective adsorbent and provide a first flush stream in line 14. The first flush stream comprising back end compounds is passed to waste disposal, or optionally sent to solvent recovery (not shown) to recover at least a portion of the polar solvent, which may be returned to the first and second simulated moving bed (SMB) zones 102 and 103, respectively, as the mobile phase desorbent following appropriate removal of the back end carotenoids and mixing with the appropriate amount of non-polar solvent, such as n-heptane to provide the required mobile phase desorbent composition with an appropriate ratio of non-polar to polar organic solvent. Preferably, the selective adsorbent in the first solid phase extraction zone is silica or alumina. More preferably, the selective adsorbent in the first solid phase extraction zone is silica having an average particle size of from 60-200 microns and a pore size of from about 55 to 65 Angstroms. The first SMB feed stream in line 12 is passed to the first SMB zone 102. A first mobile phase desorbent comprising from 80-99 parts non-polar solvent to 1 to 20 parts polar organic solvent, and more preferably, 80 to 85 parts n-heptane to 15-20 parts polar organic compound, such as ethyl-acetate, is passed to the first SMB zone 102 in line 16. The first SMB zone 102 comprises a plurality of adsorbent beds, for example at least 8 adsorbent beds, and contains a stationary phase agent which is selective for the adsorption of polar compounds, such as silica or alumina. The first SMB zone 102 is operated in a manner which provides a first extract stream in line 18 which comprises back end carotenoids, gamma-tocotrienol, delta-tocotrienol, delta-tocopherol, and gamma-tocopherol, and a first raffinate stream in line 17 comprising first mobile phase desorbent, front end carotenoids, alpha-tocopherol, and alpha-tocotrienol. For example, the first SMB zone can be operated in a 2-3-2-1 SMB cycle or configuration as described hereinabove. The first extract stream in line 18 is passed to waste disposal following solvent (n-heptane) removal, or alternatively to further processing (not shown) by passing the first extract stream to a first solvent stripping zone for the removal of at least a portion of the polar solvent and the non-polar solvent by distillation or evaporation (not shown) and the recovery of gamma-tocotrienol or delta-tocotrienol as a mixed trienol product comprising about 60 wt-% or more gamma and delta tocotrienols on a solvent free basis. More preferably, the mixed trienol product comprises about 70 wt-% or more gamma and delta tocotrienols on a solvent free basis. The first raffinate stream in line 17 is passed to a first evaporation zone 105 and therein evaporated to remove essentially all of the polar organic solvent to provide a first solvent stream in line 32 comprising polar organic solvent and an evaporated first raffinate stream in line 38, being essentially free of the polar organic solvent. The first solvent stream in line 32 is passed to a solvent recovery zone (not shown) where the composition of the first solvent stream in line 32, which should have the same composition as the first mobile phase desorbent stream in line 16, is evaluated and adjusted, if required, and recycled (not shown) to provide at least a portion of the first mobile phase desorbent stream in line 16 in order to minimize net solvent usage. Alternatively, the first solvent stream in line 32 is sent to disposal. By the term "essentially free of the polar organic solvent", it is meant that the evaporated first raffinate stream comprises less than 0.5 wt-% of the polar organic compound, such as isopropyl, ethanol, or ethyl-acetate. The evaporated first raffinate stream in line 38 is then diluted with pure n-heptane in line 36 in dilution zone 106 to provide a second SMB feed stream in line 20. Preferably, the second SMB feed stream in line 20 comprises the evaporated first raffinate stream diluted in the n-heptane to a 3 to 10 wt-% solution with pure n-heptane. More preferably, the second SMB feed stream in line 20 comprises the evaporated first raffinate stream diluted in the n-heptane to a 5 to 8 wt-% solution with pure n-heptane. The removal of the first mobile phase desorbent from the first raffinate stream and re-dilution with pure n-heptane was critical for preventing any selectivity issues which may arise in the second SMB zone. The second SMB feed stream in line 20 is passed to the second SMB zone 103. The second SMB feed stream in line 20 is passed to the second SMB zone 103, containing a plurality of adsorbent beds containing a polar compound selective stationary phase agent comprising silica or basic alumina and therein contacted with a mobile phase agent comprising a binary mixture of n-heptane and a polar organic solvent having a ratio of n-heptane to the polar organic solvent of from 90-99 parts n-heptane to 1-10 parts polar organic solvent in a front end polar compound rejection SMB cycle to provide a second raffinate stream in line 26 comprising front end carotenoids and alpha-tocopherol, and a second extract stream in line 23 comprising mobile phase agent and high purity alpha-tocotrienol and beta-tocopherol. The second extract stream in line 23 is passed to a second evaporization zone 107 to remove essentially all of the polar organic solvent as a second solvent stream in line 34 and to provide an evaporated second extract stream in line 24. The second solvent stream in line 34 is passed to a second solvent recovery zone (not shown) where the composition of the second solvent stream in line 34, which should have the same composition as the second mobile phase desorbent stream in line 22, is evaluated and adjusted, if required, and recycled (not shown) to provide at least a portion of the second mobile phase desorbent stream in line 22 in order to minimize net solvent usage. Alternatively, the second solvent stream in line 34 is sent to disposal. By the term high purity, it is meant that the second extract stream comprises between about 90 and about 99.99 wt-% alpha-tocotrienol on a solvent free basis. The evaporated second extract stream in line 24 may still comprise small amounts of impurities in the form of other tocopherols and tocotrienols. Accordingly, the evaporated second extract stream in line 24 is diluted with pure n-heptane in line 36 in a second dilution zone 108 to provide a 5-15 weight percent solution (more preferably, 10-15 weight percent solution) in the n-heptane, and the diluted evaporated second extract stream in line 25 is passed to a second solid phase extraction zone 104, containing a second selective adsorbent comprising basic alumina having an average particle size of from 30 to 60 microns and withdrawing a high purity alpha-tocotrienol product stream in line 28 having an alpha-tocotrienol purity of between about 95 and about 99.99 wt-% alpha-tocotrienol on a solvent free basis. Preferably the high purity alpha-tocotrienol is of high purity (i.e., 90, 93, 95, 96, 97, 98, 99, 99.5 wt-% on a solvent free basis). The high purity alpha-tocotrienol stream in line 28 is further processed to remove any traces of solvent such as n-heptane. Although not shown in the drawing (FIG. 1), the high purity alpha-tocotrienol stream may be purged with a pure nitrogen stream to remove any remaining solvent. The second selective adsorbent is silica or basic alumina. More preferably, the second selective adsorbent is basic alumina. It was discovered that in order to achieve the desired purity of the alpha-tocotrienol without the beta-tocopherol impurity, it was critical that the evaporated first raffinate stream and the evaporated second extract stream be essentially free of the polar organic solvent and then be diluted with pure n-heptane solvent as described hereinabove. The second raffinate stream in line 26, which comprises solvent (n-heptane), front end carotenoids and alpha-tocopherol is passed to waste disposal following solvent (n-heptane) removal, or alternatively passed to further processing (not shown) by passing the second raffinate stream to a second solvent stripping zone for the removal of at least a portion of the solvent (n-heptane) and for the recovery of an alpha-tocopherol rich product stream comprising from about 70 to about 80 wt-% alpha-tocopherol on a solvent free basis. Intermittently, the passing of the diluted evaporated second extract stream in line 25 to the second solid extraction zone 104 is terminated when the concentration of beta-tocopherol in line 28 is about 2 wt-%. At this point in the process, the second solid phase extraction zone 104, is now shown as a loaded second solid phase extraction zone 104' which still retains high purity alpha-tocotrienol. This additional alpha-tocotrienol product is recovered in a first purging step by purging the loaded second solid phase extraction zone 104' with the non-polar solvent such as n-heptane in line 36 to recover the additional high purity alpha-tocotrienol product in line 30, which can be combined with the high purity alpha-tocotrienol product in line 28 (not shown) prior to solvent removal. The loaded second solid phase extraction zone 104' now comprises the byproduct, beta-tocopherol, and is shown as byproduct zone 104". The byproduct stream in line 40 comprising beta-tocopherol is recovered by purging the byproduct zone 104" with a polar organic solvent in line 44, such as isopropanol, ethanol, or ethyl-acetate, to provide the byproduct stream comprising beta-tocopherol and polar solvent in line 40 The by-product stream in line 40, following removal of any polar organic solvent by distillation or evaporation at vacuum conditions, provides a byproduct steam composition comprising at least about 80 weight percent beta-tocopherol, on a solvent free basis.

Figure 2:
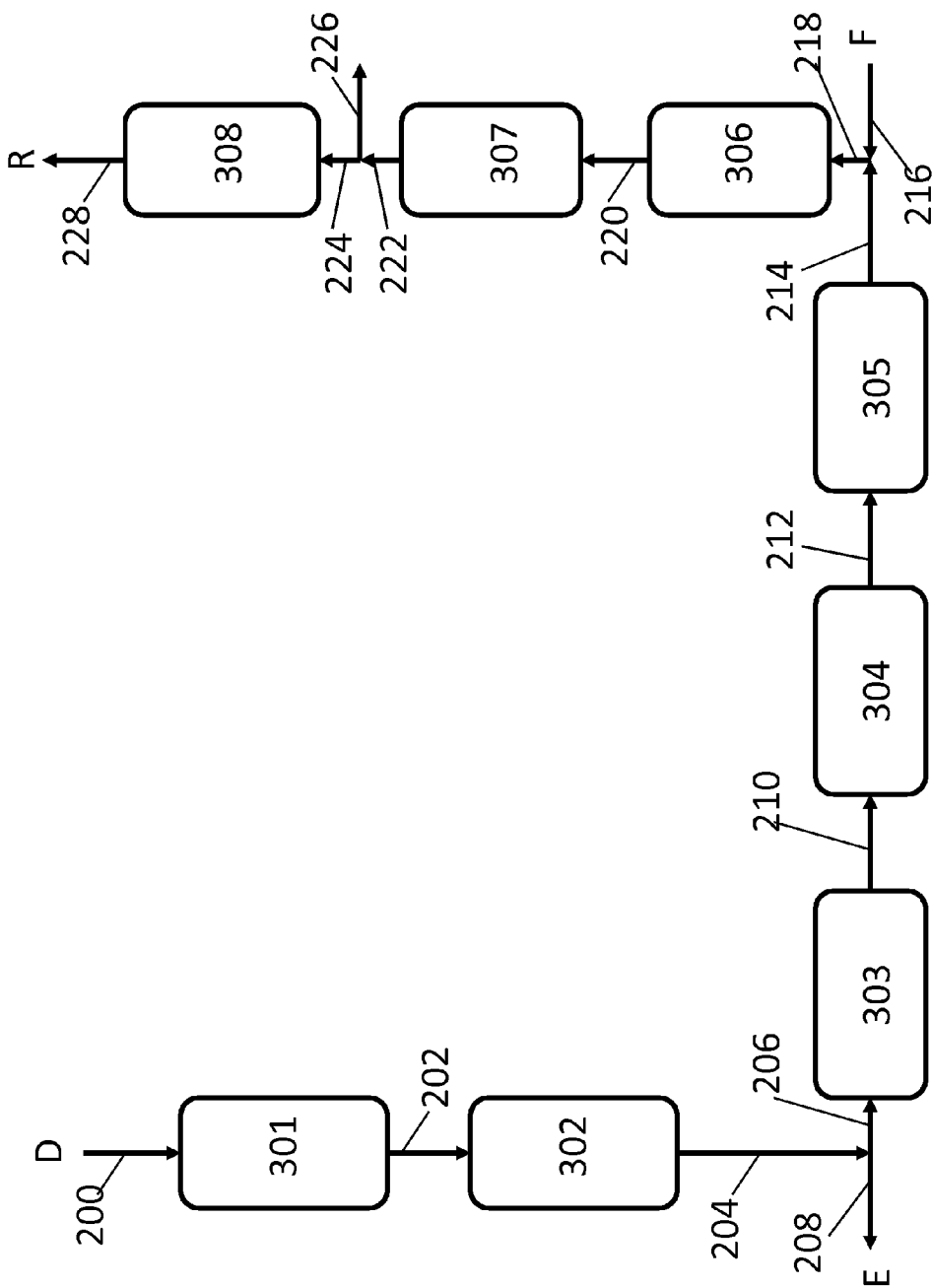
FIG. 2 is a schematic flow diagram of the SMB cycle illustrating one embodiment of the present invention.

Referring to FIG. 2, one embodiment of the simulated moving bed zones of the present invention as used in the first and second SMB zones described hereinabove are shown herein as operating in a simulated moving bed (SMB) cycle based on an eight adsorbent bed arrangement. Adsorbent beds 301, 302, 303, 304, 305, 306, 307, and 308, containing a stationary phase adsorbent as described hereinabove, are disposed in a serial configuration such that in accordance with a prearranged cycle, conduit 202 provides fluid communication between the bottom of adsorbent bed 301 with the top of adsorbent bed 302, conduits 204 and 206 provide fluid communication between the bottom of adsorbent bed 302 bed and the top of adsorbent bed 303, conduit 210 provides fluid communication between the bottom of adsorbent bed 303 with the top of adsorbent bed 304, conduit 212 provides fluid communication between the bottom of adsorbent bed 304 with the top of adsorbent bed 305, conduits 214 and 218 provide fluid communication between the bottom of adsorbent bed 305 with the top of adsorbent bed 306, conduit 220 provides fluid communication between the bottom of adsorbent bed 306 with the top of adsorbent bed 307, conduits 222 and 224 provide fluid communication between the bottom of adsorbent bed 307 with the top of adsorbent bed 308, and conduit 226 provides for the withdrawal of fluid from the bottom of adsorbent bed 307 as the primary raffinate, and line 228 provides for the withdrawal of a secondary raffinate or void volume flush of the adsorbent bed 308 which is in transition from the desorption zone to the adsorption zone. According to the prearranged SMB cycle of the present invention, an SMB zone feed stream is passed to the SMB adsorption zone in line 216 and 218 to adsorbent bed 306. A primary raffinate stream is withdrawn from adsorbent bed 307 in conduits 222 and 226, and an extract stream is withdrawn via conduits 204 and 208 from adsorbent bed 302. A mobile phase desorbent stream as described hereinabove is introduced to adsorbent bed 301 in conduit 200. In this embodiment, the adsorbent beds 301-308 are indexed according to a 2-3-2-1 SMB cycle such that at least 2 adsorbent beds (301 and 302) undergo desorption in a desorption zone, at least 3 adsorbent beds (303, 304, and 305) undergo rectification in a rectification zone, and at least 3 adsorbent beds (306, 307, and 308) undergo adsorption in an adsorption zone during the SMB cycle of the present invention. The first and second SMB zones have the same bed arrangement and employ the same 2-3-2-1 SMB cycle, but the capacities and cycle times differ. For example, for the same feed rate to each of the first and the second SMB zone, for 8 identically sized adsorbent beds in each of the SMB zones, the cycle time in the first SMB zone was about half that of the cycle time in the second SMB zone.

The following examples are provided to illustrate the present invention. These examples are shown for illustrative purposes, and any invention embodied therein should not be limited thereto.

EXAMPLES

Example 1

Pulse Test of Alpha-Tocotrienol Separation

Figure 3:
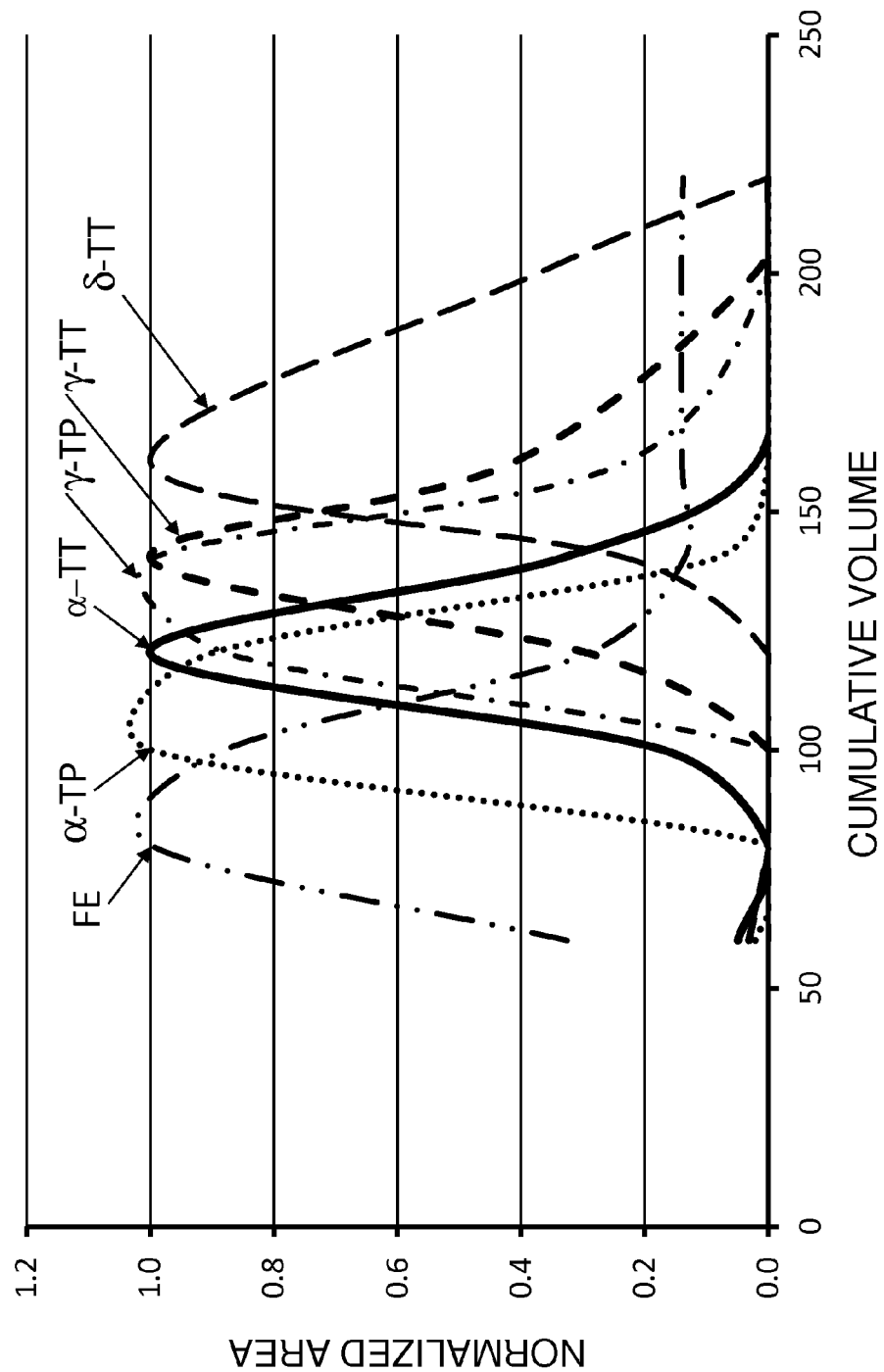
FIG. 3 is a chart of a pulse test over a silica stationary phase for a mixture of 10 wt-% crude palm oil extract dissolved in n-heptane.

A chromatographic column of 316 stainless steel and having an inside diameter of 22 mm and a length of 300 mm was prepared for high pressure liquid chromatography (HPLC) for use in establishing the elution profile of the major components of a mixture of crude palm oil extract dissolved in a solvent. The solvent was n-heptane, and the mixture comprised 10 wt-% of crude palm oil extract and the remainder being chemically pure n-heptane. The chromatographic column was filled with 60 grams of AGC Silica (Available from AGC Chemicals Americas, Inc., Exton, Pa.), a spherical highly pure (99.90 wt-% SiO2) silica particles as the stationary phase. The silica particles were in the form of beads and were about 50 microns in size and had about a 60 Angstrom pore size. A flow of mobile phase desorbent comprising a 80:20 mixture of n-heptane to ethyl-acetate at a rate of 0.2 ml/min was established in the column at an ambient temperature of about 25° C. A 3 ml aliquot of a feed mixture comprising 90 wt-% n-heptane (>99% purity) and 10 wt-% of crude palm oil extract was injected into the column and the resulting eluent fractions were collected at 2 minute intervals. The compositions were analyzed by HPLC using an AGILENT 1100 series (Available from Agilent Technologies, Santa Clara, Calif.). The results of Example 1 shown in FIG. 3 indicate a relative selectivity of alpha-tocotrienol over the mixed tocopherols. The front end carotenoids (FE) and the alpha-tocopherol ($\alpha$-TP) eluted before the alpha-tocotrienol peak ($\alpha$-TT), and the gamma-tocopherol ($\gamma$-TP), the gamma-tocotrienol ($\gamma$-TT), and delta-tocotrienol peaks ($\delta$-TT) eluted after the alpha-tocotrienol peak ($\alpha$-TT). Therefore, it was determined that an alpha-tocotrienol separation over the silica particle stationary phase in a simulated moving bed SMB process was feasible.

Example 2

Pulse Test of SILICYCLE 75-200 micron—An Irregular Silica

The pulse test of Example 1 was repeated using SILICYCLE SILICA FLASH G60, an irregular silica having a size range of from 60-200 microns and a pore size of 60 Angstroms (Available from SiliCyle, Quebec City (Quebec) CANADA) as the stationary phase agent with the a 80:20 mixture of n-heptane to ethyl-acetate as the mobile phase according to the procedure described in Example 1. The results of Example 2, as in Example 1, showed a relative selectivity of alpha-tocotrienol over the mixed tocopherols.

Example 3

Pulse Test of Alumina Basic

The pulse test of Example 1 was repeated using Alumina Basic having a particle size of from 32-63 microns as the stationary phase agent with the a 80:20 mixture of n-heptane to ethyl-acetate as the mobile phase according to the procedure described in Example 1. The results of Example 3, as in Example 1, showed a similar relative selectivity of alpha-tocotrienol over the mixed tocopherols.

Example 4

Test of Silica on Varying Mobile Phase Compositions

A chromatographic column of 316 stainless steel and having an inside diameter of 4.6 mm and a length of 150 mm was prepared for high pressure liquid chromatography (HPLC) for use in establishing the elution profile of the major components of a mixture of crude palm oil extract dissolved in a solvent. The solvent was n-heptane, and the mixture comprised 10 wt-% of crude palm oil extract and the remainder being chemically pure n-heptane. The chromatographic column was filled with 3 grams of RELIASIL Silica 5 micron (Available from Orochem Technologies, Inc., Lombard, Ill.), a spherical highly pure (99.90 wt-% SiO2) silica particles as the stationary phase. The silica particles were in the form of beads and were about 5 microns in size and had about a 90 Angstrom pore size. A flow of mobile phase desorbent comprising n-heptane and ethyl-acetate in a series of ratios ranging from 80:20 n-Heptane:Ethyl-acetate to 98:2 n-Heptane: Ethyl-acetate at a rate of 1.0 ml/min was established in the column at an ambient temperature of about 25° C. A 5 microliter aliquot of a feed mixture comprising 90 wt-% n-heptane (>99% purity) and 10 wt-% of crude palm oil extract was injected into the column and the resulting eluent fractions were analyzed on-line 290 nanometer. The compositions were analyzed directly by HPLC using an AGILENT 1100 series (Available from Agilent Technologies, Santa Clara, Calif.). The results of Example 4 are as selectivities of alpha-tocotrienol and gamma-tocotrienol, and alpha-tocotrienol and alpha-tocopherol are in Table 1. As shown in Table 1, the selectivities of the alpha-tocotrienol relative to both gamma-tocotrienol and to alpha-tocopherol are greater than 1.0 over the entire range of ratios from 80:20 to 98:2 parts n-heptane to ethyl-acetate.

TABLE 1

Selectivity between Alpha-tocotrienol between Gamma-Tocotrienol and between Alpha-Tocotrienol and Alpha-Tocopherol

| Mobile Phase Ratio of N-Heptane: Ethyl-acetate | Selectivity of Alpha-tocotrienol: Gamma-Tocotrienol | Selectivity of Alpha-tocotrienol: Alpha-Tocopherol |
|---|---|---|
| 98:02 | 2.47 | 1.32 |
| 97:03 | 1.65 | 1.30 |
| 95:05 | 1.97 | 1.32 |
| 90:10 | 1.69 | 1.33 |
| 85:15 | 1.44 | 1.29 |
| 80:20 | 1.29 | 1.40 |

Example 5

Material Balance

A high purity alpha-tocotrienol product was recovered from a crude palm oil extract using the process of the present invention. The crude palm oil extract had the composition shown in Table 2.

TABLE 2

Composition of Crude Palm Oil Extract

| Component | Wt-% |
|---|---|
| Front End Polar Components* | 12 |
| Alpha-tocopherol | 20 |
| Alpha-tocotrienol | 17 |
| Gamma-tocopherol | 3 |
| Gamma-tocotrienol | 28 |
| Beta-tocopherol | 0.5 |
| Delta-tocopherol | 3 |
| Delta-tocotrienol | 13 |
| Back End Polar Components** | trace |
| Total | 100.0 |

*Misc. Polar Components eluting before alpha-tocotrienol
**Misc. Polar Components eluting after alpha-tocotrienol According to the process as described hereinabove in FIG. 1, the crude palm oil extract was first diluted in pure n-heptane (>99 wt-% n-heptane) to a provide a feed stream comprising from 20 to 25 wt-% of the crude palm oil extract. The feed stream was passed to a first solid phase extraction zone containing a silica adsorbent to provide a first SMB feed stream. The first SMB feed stream at a feed rate of 220 ml/min and a mobile phase desorbent stream at a first desorbent rate of 2500 ml/min was passed to the first SMB zone. The SMB zone consisted of 8-152 mm by 911 mm cylindrical adsorbent beds filled with the silica adsorbent and operated in a 2-3-2-1 SMB cycle at a cycle time of about 14 to 15 minutes to provide a first raffinate stream and a first extract stream. The mobile phase consisted of a mixture of pure n-heptane and ethyl-acetate in a 80:20 weight ratio of n-heptane to ethyl-acetate. Table 3 shows the composition of the first feed, first extract and first raffinate streams on a mobile phase free basis.

TABLE 3

Composition of First SMB Streams (Exclusive of Solvent)

| Component | Feed Wt-% | Extract Wt-% | Raffinate Wt-% |
|---|---|---|---|
| Front End Polar Components* | 15.2 | 15.3 | 6.1 |
| Alpha-tocopherol | 19.1 | 5.2 | 49.4 |
| Alpha-tocotrienol | 17.7 | 3.2 | 43.4 |
| Gamma-tocopherol | 3.11 | 5.8 | 0.03 |
| Gamma-tocotrienol | 28.68 | 48.2 | 0.13 |
| Beta-tocopherol | 0.47 | 0.6 | 1.02 |
| Delta-tocopherol | .44 | 0 | 0 |
| Delta-tocotrienol | 14.2 | 21.6 | 0 |
| Back End Polar Components** | 0 | 0 | 0 |
| Total | 100.0 | | |

*Misc. Polar Components eluting before alpha-tocotrienol

The first raffinate stream was evaporated to remove a portion of the mobile phase agent and the evaporated first raffinate stream was diluted in pure n-heptane to provide a 20-25 weight percent solution in the n-heptane and at a second SMB feed rate of 220 ml/min was passed to the second SMB zone. The second SMB zone consisted of 8-152 mm by 911 mm cylindrical adsorbent beds filled with silica adsorbent. The second SMB zone was configured and operated in a 2-3-2-1 SMB cycle with a cycle time of about 28 to 30 minutes. A second desorbent agent consisted of a mixture of pure n-heptane and ethyl-acetate in a 93:7 weight ratio of n-heptane to ethyl-acetate. The second SMB zone provided second extract stream and a second raffinate stream. Table 4 shows the composition of the second feed, second extract and second raffinate streams on a mobile phase agent free basis.

TABLE 4

Composition of Second SMB Streams

| Component/Wt-% | Second SMB Feed | Second Extract | Second Raffinate |
|---|---|---|---|
| Front End Polar Components* | 6.1 | 0.4 | 46 |
| Alpha-tocopherol | 49.4 | 0.69 | 50.1 |
| Alpha-tocotrienol | 43.4 | 94.2 | 3.5 |
| Gamma-tocopherol | 0.03 | 0.14 | 0 |
| Gamma-tocotrienol | 0.13 | 0.42 | 0.13 |
| Beta-tocopherol | 3.5 | 0 | 12.8 |
| Delta-tocopherol | 0 | 0 | 0 |
| Delta-tocotrienol | 0 | 0 | 0 |
| Back End Polar Components** | 0 | 0 | 0 |
| Total | | | |

*Misc. Polar Components eluting before alpha-tocotrienol

The second extract stream was passed to a second evaporization zone and therein evaporated to remove at least a portion of the mobile phase agent to provide an evaporated second extraction stream. The evaporated second extraction stream after dilution with n-heptane to provide a 20-25 weight percent solution in the n-heptane was passed to a second solid phase extraction zone containing basic alumina to provide an alpha-tocotrienol product stream. The resulting composition of the alpha-tocotrienol product stream is shown in Table 5 following removal of the n-heptane by distillation.

TABLE 5

Composition of Alpha-Tocotrienol

| Component | Weight Percent |
|---|---|
| Front End Polar Components* | 0.3 |
| Alpha-tocopherol | 0.6 |
| Alpha-tocotrienol | 97.6 |
| Gamma-tocopherol | 0.11 |
| Gamma-tocotrienol | 0.23 |
| Beta-tocopherol | 0.8 |
| Delta-tocopherol | 0 |
| Delta-tocotrienol | 0 |
| Back End Polar Components** | 0 |
| Total | |

*Misc. Polar Components eluting before alpha-tocotrienol

The resulting alpha-tocotrienol was about 98 percent pure with an overall recovery in excess of 90 percent. Furthermore, the by-product stream following removal of any mobile phase desorbent by distillation are about 80 weight percent in purity.

Although the systems and processes described herein have been described in detail, it should be understood that various changes, substitutions, and alterations can be made without departing from the spirit and scope of the invention as defined by the following claims. Those skilled in the art may be able to study the preferred embodiments and identify other ways to practice the invention that are not exactly as described herein. It is the intent of the inventors that variations and equivalents of the invention are within the scope of the claims, while the description, abstract and drawings are not to be used to limit the scope of the invention. The invention is specifically intended to be as broad as the claims below and their equivalents.

We claim:

1. A continuous simulated moving bed (SMB) separation process for the production of a high purity alpha-tocotrienol product stream from crude palm oil extract, said process comprising:
   a. diluting the crude palm oil extract comprising front end carotenoids, alpha-tocopherol, alpha-tocotrienol, gamma-tocopherol, gamma-tocotrienol, beta-tocopherol, delta-tocopherol, delta-tocotrienol, and back end carotenoids in a non-polar solvent to provide a feed stream comprising 20 to 25 wt-% of the crude palm oil extract,
   b. passing the feed stream to a first solid phase extraction zone and therein contacting a first solid phase adsorbent comprising silica for the adsorption of back end carotenoids to remove at least a portion of the back end carotenoids from the feed stream provide a first SMB feed stream;
   c. passing the first SMB feed stream to a first SMB zone comprising a plurality of adsorbent beds, each adsorbent bed containing a stationary phase agent comprising silica or alumina and passing a first mobile phase desorbent stream comprising non-polar solvent and a polar organic solvent in a first SMB zone ratio of from 80-99 parts non-polar solvent: 1-20 parts of said polar organic solvent to the first SMB zone to provide a first extract stream comprising non-polar solvent, polar organic solvent, back end carotenoids, gamma-tocotrienol, delta-tocotrienol, and gamma-tocopherol, and a first raffinate stream comprising non-polar solvent, organic polar solvent, front end carotenoids, alpha-tocopherol and alpha-tocotrienol;
   d. passing the first raffinate stream to a first evaporization zone to remove essentially all of the polar organic solvent from the first raffinate stream to provide a first solvent stream comprising the polar organic solvent and an evaporated first raffinate stream and diluting the evaporated first raffinate stream with non-polar solvent to provide a second SMB feed stream comprising 3 to 10 wt-% of the evaporated first raffinate stream in non-polar solvent;
   e. passing the second SMB feed stream to a second SMB zone comprising a plurality of adsorbent beds, each adsorbent bed containing a second stationary phase agent comprising silica or alumina and passing a second mobile phase desorbent stream comprising non-polar solvent and the polar organic solvent in a second SMB zone ratio of from 90-99 parts non-polar solvent: 1-10 parts of said polar organic solvent to the second SMB zone to provide a second raffinate stream comprising non-polar solvent, polar organic solvent, front end carotenoids, alpha-tocopherol, and to provide a second extract stream comprising non-polar solvent, polar organic solvent and alpha-tocotrienol;
   f. passing the second extract stream to a second evaporization zone to remove essentially all of the polar organic solvent from the second extract stream to provide a second solvent stream comprising the polar organic solvent and an evaporated second extract stream and diluting the evaporated second extract stream with non-polar solvent to provide a diluted evaporated second extract stream comprising 5 to 15 wt-% of the evaporated second extract stream in non-polar solvent; and,
   g. passing the diluted evaporated second extract stream to a second solid phase extraction zone and therein contacting a basic alumina adsorbent to provide a first high purity alpha-tocotrienol stream comprising the non-polar solvent and alpha-tocotrienol;

h. terminating the passing of the diluted evaporated second extract stream to the second solid phase extraction zone and purging the second solid phase extraction zone in a first purging step with the non-polar solvent to provide a second high purity alpha-tocotrienol stream comprising the non-polar solvent and alpha-tocotrienol;

i. terminating the first purging step and purging the second solid phase extraction zone in a second purging step with the polar solvent to provide a byproduct stream comprising beta-tocopherol; and, j. combining the first and second high purity alpha-tocotrienol streams and removing the non-polar solvent to provide the high purity alpha-tocotrienol product stream having an alpha-tocotrienol purity of greater than or equal to 95 wt-% on a solvent free basis, wherein the non-polar solvent is hexane or n-heptane, and the polar organic solvent is isopropanol, ethanol, or ethyl-acetate.

2. The process of claim 1, wherein the first mobile phase desorbent and the second mobile phase desorbent stream comprise the same ratio of non-polar solvent to polar organic solvent.

3. The process of claim 1, wherein the first mobile phase desorbent stream and the second mobile phase desorbent stream comprise different ratios of non-polar solvent to polar organic solvent.

4. The process of claim 1, wherein the first mobile phase desorbent stream comprises a ratio of n-heptane to polar organic solvent of from 80-85 parts n-heptane to 20-15 polar organic solvent, and the second mobile phase desorbent stream comprises a ratio of n-heptane to polar organic solvent of from 90-99 parts n-heptane to 1-10 polar organic solvent ratios of n-heptane to polar organic solvent.

5. The process of claim 1, wherein the second mobile phase desorbent stream is a binary mixture of n-heptane and the polar organic solvent in a ratio of 90:10, 91:9, 92:8, 93:7, 94:6, or 95:5 parts n-heptane to parts polar organic solvent.

6. The process of claim 1, wherein the non-polar solvent is n-heptane and the polar organic solvent is ethyl-acetate.

7. The process of claim 1, wherein the mobile phase desorbent stream in the second SMB zone is a binary mixture of n-heptane and ethyl-acetate in a ratio of 93:7 parts n-heptane to parts ethyl-acetate.

8. The process of claim 1, wherein the first solid phase adsorbent selective for the adsorption of back end carotenoids is silica having an average particle size of from 60-200 microns and a pore size of from about 55 to 65 Angstroms.

9. The process of claim 1 wherein the first and second SMB zones are operated in a 2-3-2-1 simulated moving bed cycle.

10. The process of claim 1, wherein the high purity alpha-tocotrienol stream having an alpha-tocotrienol purity greater than or equal to 97 wt-% on a solvent free base.

11. The process of claim 1, wherein the first and the second SMB zones comprise at least 8 adsorbent beds.

12. The process of claim 1, further comprising recycling at least a portion of the first solvent stream to step (c) of claim 1 to provide at least a portion of the first mobile phase desorbent stream.

13. The process of claim 1, further comprising recycling at least a portion of the second solvent stream to step (e) of claim 1 to provide at least a portion of the second mobile phase desorbent stream.

14. The process of claim 1, further comprising passing the first extract stream to a first solvent stripping zone to remove at least a portion of non-polar solvent and polar organic solvent to provide a mixed trienol product comprising about 60 wt-% or more gamma and delta tocotrienols on a solvent free basis.

15. The process of claim 1, further comprising passing second raffinate stream to a second solvent stripping zone to remove at least a portion of the solvent and to provide an alpha-tocopherol rich product stream comprising from about 70 to about 80 wt-% alpha-tocopherol on a solvent free basis.

* * * * *